US012605456B2

(12) United States Patent
Goldfarb et al.

(10) Patent No.: US 12,605,456 B2
(45) **Date of Patent: *Apr. 21, 2026**

(54) COMPOSITION AND METHOD FOR HIP1-TARGETING INHIBITOR COMPOUNDS

(71) Applicant: Utah Valley University, Orem, UT (US)

(72) Inventors: Nathan E. Goldfarb, Orem, UT (US); Andrew Abell, Adelaide (AU); Nicholas Schumann, Adelaide (AU); Borja Lopez Perez, Santiago de Compostela (ES)

(73) Assignee: Utah Valley University, Orem, UT (US)

( * ) Notice: Subject to any disclaimer, the term of this patent is extended or adjusted under 35 U.S.C. 154(b) by 108 days.

This patent is subject to a terminal disclaimer.

(21) Appl. No.: 17/827,700

(22) Filed: May 28, 2022

(65) Prior Publication Data

US 2023/0001000 A1 Jan. 5, 2023

Related U.S. Application Data

(60) Provisional application No. 63/217,172, filed on Jun. 30, 2021.

(51) Int. Cl.

| | |
|---|---|
| ***A61K 38/00*** | (2006.01) |
| ***A61K 47/66*** | (2017.01) |
| ***A61P 31/06*** | (2006.01) |
| ***C07K 5/08*** | (2006.01) |
| ***C07K 7/06*** | (2006.01) |

(52) U.S. Cl.

CPC .............. *A61K 47/66* (2017.08); *A61P 31/06* (2018.01)

(58) Field of Classification Search

CPC ......... A61K 38/00; A61K 47/66; A61P 31/06; C07K 5/0812; C07K 7/06; C07K 5/08

See application file for complete search history.

(56) References Cited

PUBLICATIONS

Stutz et al., "Superparamagnetic core-shell nanoparticles as solid supports for peptide synthesis," Chem. Commun., 2012, 48: 7176-7178. (Year: 2012).*

Cbz-Phe-Lys-Leu-CO2Me from PubChem, https://pubchem.ncbi.nlm.nih.gov/compound/Cbz-Phe-Lys-Leu-CO2Me, pp. 1-8. Created Dec. 14, 2025. (Year: 2025).*

* cited by examiner

*Primary Examiner* — Julie Ha

(74) *Attorney, Agent, or Firm* — Workman Nydegger

(57) ABSTRACT

Provided herein is an inhibitor compound targeting Hip1, with the inhibitor compound comprising a tripeptide targeting sequence that directs the compound to the active site of Hip1 and a C-terminal electrophilic warhead conjugated to the targeting sequence, the warhead configured to inactive the enzyme.

20 Claims, 4 Drawing Sheets
(1 of 4 Drawing Sheet(s) Filed in Color)

COMPOSITION AND METHOD FOR HIP1-TARGETING INHIBITOR COMPOUNDS

CROSS-REFERENCES TO RELATED APPLICATIONS

This application claims priority to United States Provisional Patent Application No. 63/217,172 entitled "COMPOSITION AND METHOD FOR HIP1-TARGETING INHIBITOR COMPOUNDS" and filed on Jun. 30, 2121 for Nathan E. Goldfarb, which is incorporated herein by reference.

FIELD OF THE INVENTION

This invention relates to molecular targeting and more particularly relates to Hip1 inhibitor targeting drugs including for tuberculosis treatment.

BACKGROUND

According to the World Health Organization, in 2018, 1.5 million people died from *Mycobacterium tuberculosis* (Mtb) (including 251,000 people with HIV). New drugs for the treatment of Tuberculosis (TB) are direly needed. This is due to the evolution of drug resistant strains of Mtb, the causative agent of TB. Also, many of the current FDA approved drugs used to treat drug resistant strains of TB are injectables, have toxic side effects, and require a six month treatment regimen. Therefore, a need exists for a therapeutic compound narrowly targeting Mtb for an effective and rapid course of treatment. Beneficially, such a compound would be free of toxic side effects.

SUMMARY OF THE INVENTION

The foregoing discussion illustrates that a need exists for an effective, short-term treatment for Mtb, the treatment being free of toxic side effects. The present invention has been developed in response to the present state of the art, and in particular, in response to the problems and needs in the art that have not yet been fully solved by currently available Mtb treatments. Accordingly, the present invention has been developed to provide a class of inhibitors of Hydrolase important for pathogenesis (Hip1), a drug target that overcomes many or all of the above-discussed shortcomings in the art.

Reference throughout this specification to features or similar language does not imply that all of the features that may be realized with the present invention should be or are in any single embodiment of the invention. Rather, language referring to the features is understood to mean that a specific feature or characteristic described in connection with an embodiment is included in at least one embodiment of the present invention. Thus, discussion of the features and characteristics, and similar language, throughout this specification may, but does not necessarily, refer to the same embodiment.

Furthermore, the described features, and characteristics of the invention may be combined in any suitable manner in one or more embodiments. One skilled in the relevant art will recognize that the invention can be practiced without one or more of the specific features or characteristics of a particular embodiment. In other instances, additional features and characteristics may be recognized in certain embodiments that may not be present in all embodiments of the invention. These features and characteristics of the present invention will become more fully apparent from the following description and appended claims or may be learned by the practice of the invention as set forth hereinafter.

Provided herein is a novel class of potent inhibitors of Hip1, a novel cocrystal structure of a potent Hip1-directed inhibitor bound to Hip1, and a novel chromogenic substrate for Hip1. Hip1 is an Mtb serine hydrolase/protease that has emerged as a promising drug target for the development of novel TB drugs. Hip1 is an Mtb cell wall-associated serine hydrolase that plays an important role in the pathogenic strategies of Mtb cell envelope maintenance and the dampening of host cell proinflammatory responses. Functional studies identify Hip1 as a target for drug discovery. Mice infected with a Hip1 transposon mutant strain survive significantly longer than wild-type Mtb-infected mice and exhibit mild lung immunopathology despite high bacterial burdens (1,2).

The illustrated embodiment of the class of Hip1 inhibitor compounds including NS-049-2, a low molecular weight (696.72 g/mole), potent inhibitor ($K_i$=309±15 pM) of its drug target, Hip1. To date, no other drug-like, tight binding inhibitors target Hip1. As a result, antibiotic resistance has not evolved against Hip1-directed therapeutics.

Further provided herein is a class of compounds for the inhibition of Hip1, the compounds comprising a tripeptide targeting sequence, Phe-Lys-Leu, that directs the compound to the active site of Hip1; and a C-terminal alpha-keto methyl ester electrophilic warhead conjugated to the targeting sequence, the warhead configured to inactivate the enzyme. In some embodiments the compound comprises:

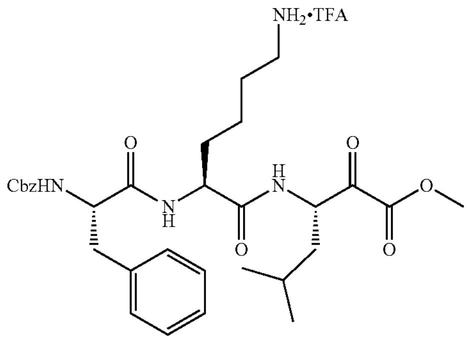

Also provided are position 1 (P1) derivatives of the compound of comprising Cbz-Phe-Lys-Gln-$COCO_2Me$, Cbz-Phe-Lys-Gln lactam-$COCO_2Me$, Cbz-Phe-Lys-Asn-$COCO_2Me$, Cbz-Phe-Lys-Glu-$COCO_2Me$, Cbz-Phe-Lys-Val-$COCO_2Me$, and Cbz-Phe-Lys-(X)—$COCO_2Me$, where (X)=any amino acid, amino acid derivative, or chemistry.

Further provided here are P3 derivatives of the compound comprising Cbz-Tyr-Lys-Leu-$COCO_2Me$, Cbz-Nle-Lys-Leu-$COCO_2Me$, and Cbz-(X)-Lys-Leu-$COCO_2Me$; where (X)=any amino acid, amino acid derivative, or chemistry.

In certain embodiments P1 and P3 derivatives comprise Cbz-(Xn+1)-Lys-(X)—$COCO_2Me$, where (Xn+1) and (X)=any amino acid(s), amino acid derivative(s), or chemistry (ies). Truncated Derivatives may comprise one or more of Cbz-Leu-$COCO_2Me$, Cbz-X—$COCO_2Me$, where (X)=any amino acid, amino acid derivative, or chemistry, Cbz-Lys-Leu-$COCO_2Me$, and Cbz-Lys-X—$COCO_2Me$, where (X)=any amino acid, amino acid derivative, or chemistry.

N-terminal Lengthened Derivatives as provided herein may comprise Cbz-$(X)_{n+1}$-Phe-Lys-Leu-$COCO_2Me$; (where $(X)_{n+1}$=any amino acid(s), amino acid derivatives, or chemistries.

Also provided herein are Protecting Group Derivatives comprising (Z)—$(X)_{n+1}$—(X)-Lys-(X)—$COCO_2Me$, where (Z)=any protecting group, $(X)_{n+1}$=any amino acid(s), amino acid derivatives, and (X)=any amino acids, amino acid derivatives, or chemistries. In certain embodiments Protecting Group Derivatives comprise Cbz-Phe-Lys-Leu-pNa (pNa=paranitroanilide) or derivatives of this compound including conjugated to various chromophores, fluorophores, antibodies, nanobodies, or other reporter groups for the design of novel enzymatic activity assays, serine protease purification methods, molecular probes for the detection of novel serine/threonine proteases, and rapid diagnostic tests for the presence of Mtb in patients.

Also provided herein are Electrophilic Warhead Derivatives comprising (Z)—$(X)_{n+1}$—(X)-Lys-(X)—(Y), where (Y)=any electrophilic group capable of forming a covalent attachment to active site Ser228 of Hip1, where (Z)=any protecting group, $(X)_{n+1}$=any amino acid(s), amino acid derivatives, and (X)-any amino acids, amino acid derivatives, or chemistries.

Additionally provided herein are methods for purification of Hip1 and the methods for cocrystallization Hip1 bound with NS-049-2, as well as the X-ray cocrystal structure of Hip1 bound with NS-049-2.

The compounds and derivatives herein provided may be used to treat at least tuberculosis, as molecular probes for the detection of serine/threonine proteases involved in pathophysiological processes, as a diagnostic assay for the detection of Mtb including from patient sputum samples and as a booster to the BCG vaccine.

In some embodiments the compounds herein are disclosed as a booster to the BCG vaccine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided. One skilled in the relevant art will recognize, however, that the invention can be practiced without one or more of the specific details, or with other methods, components, materials, and so forth. In other instances, structures, materials, or operations that are known in the art are not shown or described in detail to avoid obscuring aspects of the invention.

With a global market in the billions of dollars, FDA approved protease inhibitors have been very successful in treating a number of diseases including the Human Immunodeficiency Virus, Type 2 diabetes, Hepatitis, and obesity, to name a few. One drug development strategy is to design a compound comprising a moiety that targets the compound to the protease drug target. Conjugated to the targeting moiety is a "warhead" that inactivates the enzyme. An example of this approach is the FDA approved protease inhibitor, Bortezomib (Velcade; Takeda) which is indicated for the treatment of multiple myeloma and mantle cell lymphoma. It contains a peptidomimetic targeting sequence conjugated to a boronic acid "warhead" that inactivates the catalytic threonine residue of its target, the 26 S proteasome.

Figure 1:
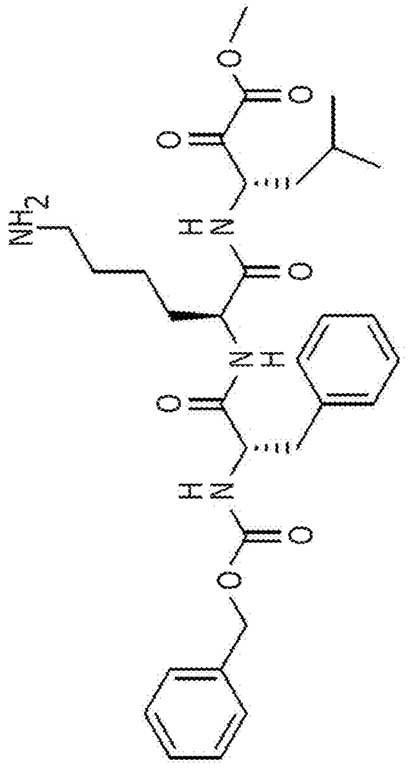
FIG. 1 depicts the structure of the inhibitor compound as determined by NMR.

FIG. 1 is a schematic line drawing depicting the structure of the illustrated embodiment of the inhibitor compound provided herein. The illustrated inhibitor compound is a potent inhibitor ($K_i$=309±15 pM) of Hip1. The inhibitor compound contains a tripeptide targeting sequence, Phe-Lys-Leu, that directs the compound to the active site of Hip1. A C-terminal alpha-keto methyl ester electrophilic warhead is conjugated to the targeting sequence. The warhead acts to quiesce the activity of the active site serine 228 residue of the enzyme, thus rendering the drug target inactive.

Advantages of this compound include its potency for Hip1 ($K_i$=309±15 pM), low molecular weight (696.72 g/mole), and its drug target, Hip1. To date, no other existing drug-like, tight binding inhibitors target Hip1. As a result, antibiotic resistance has not currently evolved against Hip1-directed therapeutics. Additionally, inhibition of Hip1 may boost the host's immune response to help clear the infection. No other anti-TB drug on the market uses this strategy to promote bacterial clearance. Furthermore, since Hip1 plays an important role in Mtb cell envelop maintenance, using NS-049-2 in conjunction with current FDA approved antibiotics may result in greater bacterial clearance efficacy. According to a recent report an Mtb transposon mutant of Hip1 exhibits severe growth attenuation in the presence of 0.5 μg/mL of ethambutol, which affected the growth of WT Mtb only marginally. This mutant also showed increased sensitivity to the antibiotics meropenem, vancomycin, and rifampicin. This indicates that inhibition of Hip1 may result in reduced Mtb fitness at partial inhibitory antibiotic concentrations. Therefore, such Mtb treatment regimens may require lower concentrations of antibiotics and/or a reduced treatment time, potentially increasing patient compliance and reducing toxic side effects. It should be noted that the use of multiple drugs (combination therapy) is a very successful approach in treating a number of bacterial, viral, fungal, and parasitic infections.

Figure 2A:
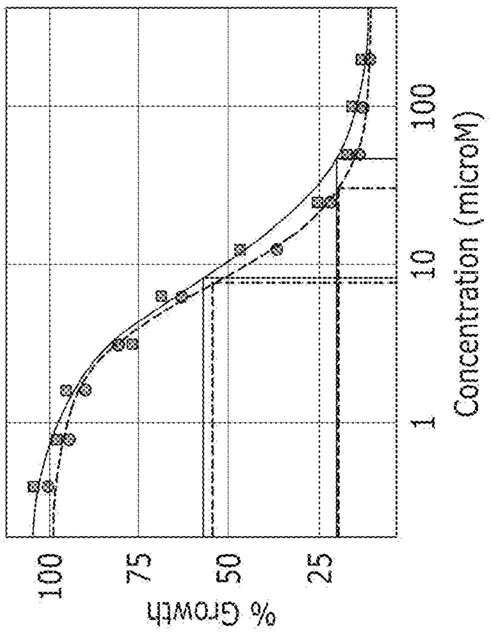
FIG. 2A shows that the inhibitor kills *Mycobacterium tuberculosis* in liquid culture in a direct killing assay with an MIC=1.32±1.4 M.

FIG. 2A is a direct killing assay showing the efficacy of the inhibitor against Mtb grown in liquid culture. The inhibitor kills Mtb with an MIC=1.32±1.4 μM. MICs were performed as described in Ollinger et al., 2013.

Figure 2B:
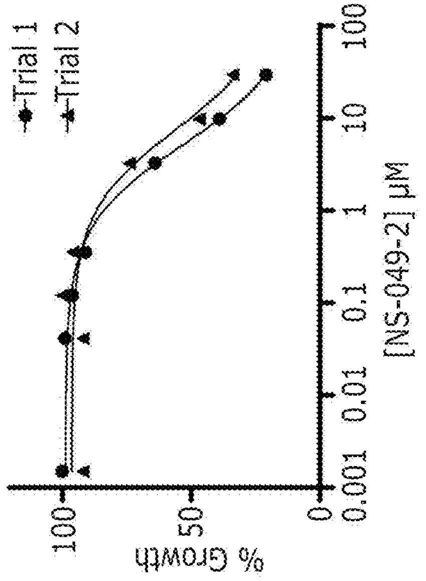
FIG. 2B shows that the inhibitor inhibits intracellular growth of *Mycobacterium tuberculosis* in its host cell, the macrophage, with an IC50=6.3±1.1 μM.

FIG. 2B shows growth inhibition of Mtb when tested in an intracellular RAW macrophage assay. RAW macrophages were infected with Mtb overnight and then treated with the inhibitor at various concentrations for seven days at which time the cytotoxicity of the inhibitor on Mtb was assessed, as previously mentioned. The inhibitor has an IC50=6.3±1.1 μM.

Figure 2C:
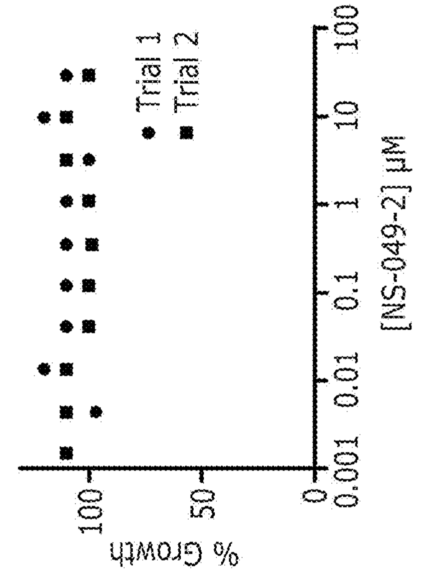
FIG. 2C shows that the inhibitor exhibits minimal cytotoxicity with RAW macrophages.

FIG. 2C shows RAW macrophages dosed with various concentrations of the inhibitor. Importantly, the compound shows minimal cytotoxicity towards RAW macrophages, with a TC50 value>100 μM.

Figure 2D:
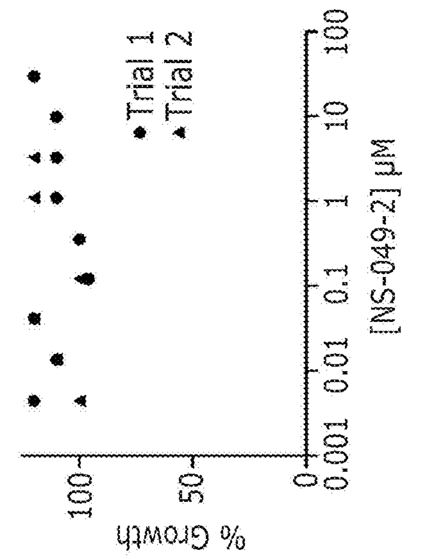
FIG. 2D shows that the inhibitor exhibits minimal cytotoxicity with HepG2 hepatocytes.

FIG. 2D shows plot of HepG2 hepatocytes versus the concentration of the inhibitor. Importantly, the compound shows minimal cytotoxicity towards HepG2 hepatocytes, with a TC50 value>100 μM.

FIGS. 3A to 3D illustrate the three-dimensional atomic X-ray cocrystal structure of Hip1 bound with the compound herein. Inspection of the structure reveals that the compound forms a covalent interaction with the active site Ser228 of Hip1, thus rendering the enzyme inactive. This constitutes a novel ligand binding mode in the active site of Hip1.

Figure 3A:
FIG. 3A is the 2.7 Å X-Ray cocrystal structure of the inhibitor compound (green sticks) herein covalently bound in the active site of Hip1.

FIG. 3A illustrates the 2.7 Å cocrystal structure of Hip1 (blue ribbon) covalently bound with the inhibitor (green sticks). The amino acid residues composing the catalytic triad of Hip1 are rendered as yellow sticks.

Figure 3B:
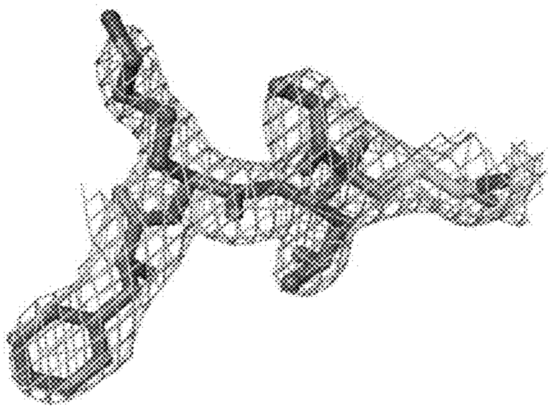
FIG. 3B shows well defined electron density (light blue chicken-wire) for the inhibitor (green sticks) covalently bound to the active site serine 228 of Hip1.

FIG. 3B illustrates the well-defined electron density (light blue chicken wire; σ level=1.0) for the inhibitor (green sticks) covalently bound to the active site Ser228 (yellow sticks) of Hip1, thus inactivating the enzyme. The absence of electron density for the Cbz protecting group suggests that it is disordered in the structure.

Figure 3C:
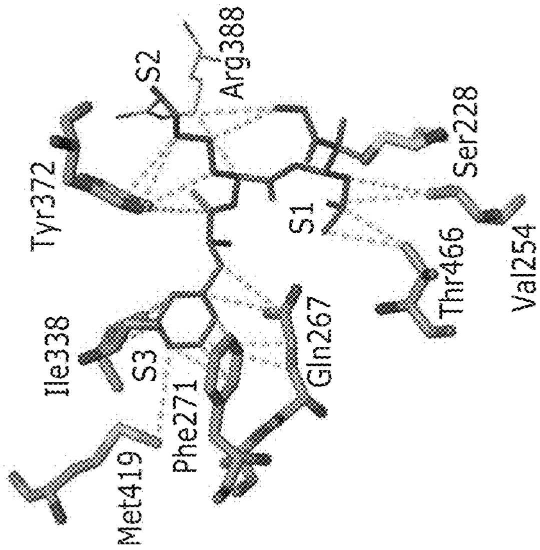
FIG. 3C shows van der Waals interactions (yellow dashes) that stabilize the inhibitor in the active site cleft of Hip1. The sidechains of the inhibitor fit into their respective pockets, labeled S1-S3, in the active site.

FIG. 3C illustrates the binding mode of the inhibitor (green sticks) in the active site of Hip1. Active site residues that make extensive van der Waals (vdw) interactions (yellow dashes) are rendered as orange sticks. Nonpolar contacts within 4.2 Å were assigned as vdw interactions. The inhibitor is stabilized in the active site through extensive vdw interactions. The active site Ser228 is colored yellow.

Figure 3D:
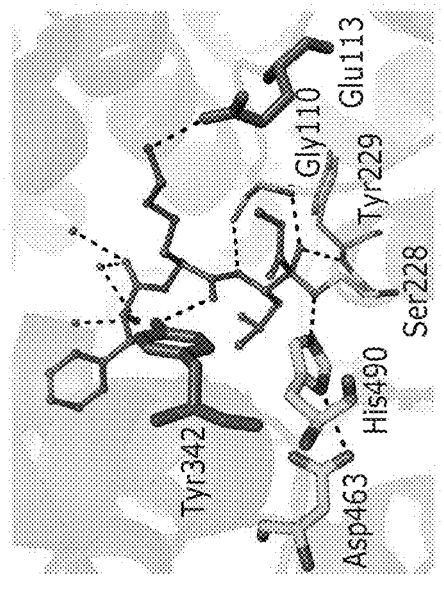
FIG. 3D shows polar interactions (black dashes) that stabilize the inhibitor (green sticks) in the active site cleft of Hip1. Water molecules are rendered as red spheres.
Figure 4:
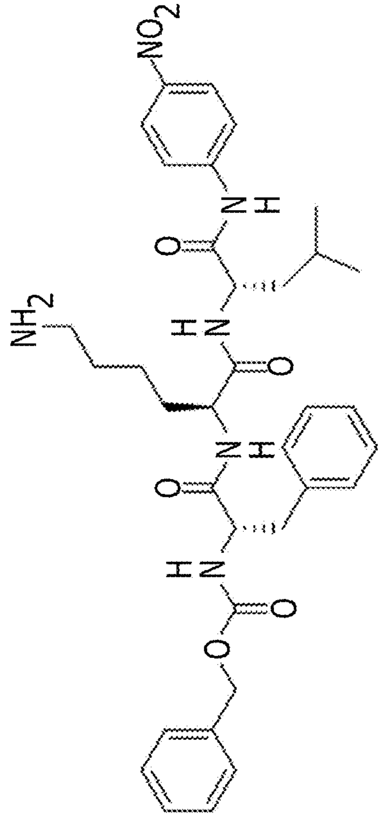
FIG. 4 shows the line structure for the novel Hip1 chromogenic substrate determined by NMR.

FIG. 3D illustrates the polar interactions (black dashes) made between the inhibitor (green sticks) and the active site residues of Hip1 (yellow, orange and blue sticks) and water molecules (red spheres). The salt bridge between P2 Lys of the inhibitor and the carboxylate of Glu113 explains the pronounced selectivity for Lys observed in substrate profiling experiments (Lentz et al., 2016);

FIG. 4 illustrates the line structure of the substrate analogue derived from the inhibitor ($K_m$=1.2±0.23 μM; data not shown). The novel chromogenic Hip1 substrate is useful for enzymatic characterization and detection of Hip1. Upon Hip1-dependent cleavage of the peptide bond between P1 leucine and the para-nitroanalide group, there is an increase in absorbance at 405 nm as detected by a spectrophotometer or plate-reader.

The inhibitor compound herein exhibits high potency for Hip1 ($K_i$=309±15 pM) and has the advantage of low molecular weight (696.72 g/mole). Additionally, the compound herein may be a reversible inhibitor. Pharmaceutical companies historically prefer to develop reversible inhibitors rather than irreversible inhibitors, as reversible inhibitors typically exhibit lower toxicity in the case of off-target binding.

This disclosure, and the supporting work represent the first crystallographic determination of a ligand binding mode in the active site of Hip1. Such an atomic roadmap of the Hip1 active site opens the way to populate this novel class of Hip1 inhibitor compounds and to refine inhibitor compounds to diminish any pharmaceutical liabilities (structure-based refinement). The inhibitor compound class herein represents a novel class of compounds that may be translated into a new drug useful for the treatment of Tuberculosis.

Rapid diagnosis of active TB in patients with negative sputum smears for acid fast bacteria may enable prompt, highly accurate identification of drug-resistant strains of *M. tuberculosis*. The inhibitor compound class herein or its derivatives may be used to develop a diagnostic test for the presence of Mtb in patient sputum samples. The compound herein or its derivatives represent scaffolds for the development of novel molecular probes useful for the detection of Mtb in patients. For example, an ELISA assay may be developed predicated on an antibody conjugated to the compound herein or its derivatives. If Mtb is present in the patient's sputum, the inhibitor-antibody probe will bind to Hip1 on the surface of Mtb. A secondary antibody is then added to generate a detectable signal. Variations of this assay may utilize other binding systems, for example the biotin-streptavidan system.

Rapid, field-ready assays may also benefit from the potency of the novel, chromogenic substrate Cbz-Phe-Lys-Leu-paranitroanalide ($K_m$=1.2±0.23 μM) described herein. Upon Hip1-dependent cleavage of the Leu-pNa bond, there is an increase in absorbance at 405 nM. Patient sputum samples positive for TB will contain Hip1, thus will react with the substrate to yield a change in absorbance which can be read on a portable spectrophotometer. Nonspecific cleavage of the substrate can be mitigated by the inclusion of protease inhibitors that do not inhibit Hip1 but do inhibit other proteases.

Finally, the inhibitor compound herein or its derivatives may be used as molecular probes useful for the discovery of other protease drug targets for Tuberculosis, as well as probes for serine/threonine proteases involved in the pathologies of other diseases. The inhibitor compound herein may also be useful as a booster for the bacilli Calmette-Guerin (BCG) vaccine which is has variable efficacy (0-80%) in preventing pulmonary TB (3). Since Hip1 plays a role in suppression of the host's immune response, the compound herein may serve to boost a patient's immune response when given in concert with the BCG vaccine, thus increasing the efficacy of the vaccine.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

EXAMPLES

Example 1. Recombinant Expression and Purification of Hip1

An N-terminally truncated recombinant Hip1 was generated using PCR deletion mutagenesis using a full length clone of Hip1 as template DNA. The truncated gene was subcloned into the glutathione S-transferase (GST) expression vector, pGEX-6P-1 (Amersham Biosciences). Overexpression of the Hip1-GST fusion protein was achieved in *E. coli* BL21 DE3 cells, cells lysed by sonication, and the fusion protein harvested as insoluble inclusion bodies. Using a modified method of Westling et al. the inclusion bodies were solubilized at 1 mg/mL in 8 M urea containing 0.05 M CAPS, 0.005 M EDTA and 0.18 M beta-mercaptoethanol with stirring at 25° C. for 45 minutes. To remove insoluble material, the mixture was centrifuged at 17,500×g for 30 min at 25° C. The clarified material was refolded by dialysis against 5.7× its volume of 0.05 M Tris-HCl, 0.005 M EDTA, 2 mM reduced glutathione, 0.4 mM oxidized glutathione, pH 7.3, at 4° C. with stirring. The dialysis buffer was replaced with fresh refolding buffer after 2 hours and protein was let refold for another 2 days. To concentrate the Hip1-GST fusion protein, it was centrifuged 20-30 min, 30,000×g, 4° C., and loaded onto 5×5 mL HiTrap Q FF columns equilibrated in 20 mM Tris-HCl, 10 mM NaCl, pH 8 (Buffer A). The column was washed at 1 mL/min for 70 min with Buffer A followed by a gradient elution of 10-100% Buffer B (20 mM Tris-HCl, 1.5 M NaCl, pH 8). To cleave the Hip1-GST fusion protein, 330 Units PreScission Protease® (Genscript) was added to 33 mg fusion protein in 20 mM Tris, 250 mM NaCl, pH 7.5, 1 mM DTT, 1 mM EDTA, 1% Tween 20 in a final volume of 4.8 mL. The reaction was rotated overnight at 4° C. N-terminal sequencing of recombinant Hip1 following PreScission Protease® cleavage indicates that the PreScission Protease® cleaves the fusion protein at the correct processing site yielding the expected N-terminus of Hip1: NH2-GPLG. To separate Hip1 from GST, the PreScission Protease® reaction was dialyzed against 4 L of 20 mM Tris-HCl, 10 mM NaCl, pH 8 for 2-4 hours, 4° C. then exchanged with fresh dialysis buffer and let dialyze overnight. The dialysate was applied to 5×5 mL HiTrap Q FF columns equilibrated in 20 mM Tris-HCl, 150 mM NaCl, pH 8 (Buffer A), 4° C. The column was washed at 1 mL/min for 120 min with Buffer A followed by a linear gradient elution of 0-100% Buffer B (20 mM Tris-HCl, 1.5 M NaCl, pH 8) over 280 min. The Hip1 containing peak was concentrated to 13 mg/mL and applied to HiPrep 16/60 Sephacryl S-100 HR size exclusion column (GE Healthcare) to separate folded from misfolded and aggregated Hip1. Protein molecular weight and purity was assessed by SDS-PAGE.

Example 2. Cocrystallization of Hip1-Inhibitor Complex and X-Ray Structure Solution Hip1 was concentrated to approximately 10 mg/mL as determined by Bradford assay, using an Amicon Ultra-15 kDa MWCO spin concentrator (Millipore). To complex Hip1 with the inhibitor (NS-049-2), an approximate 1:1 molar ratio of inhibitor dissolved in 100% DMSO was added to concentrated Hip1 with a final DMSO concentration of 2%. The complex was incubated on ice, overnight, then centrifuged at 14,000 rpm, 4° C. to remove precipitated protein. Crystal trials were set up using the hanging drop method with 4 ul drops, 2 mL mother liquor at 25° C. A fine screen of HR2-122 #15 (0.17 M ammonium sulfate, 0.085 M Na cacodylate trihydrate, pH 6.5, 25.5% w/v PEG 8,000, 15% v/v glycerol; Hampton Research) was conducted to determine optimal precipitant conditions. Large rods appeared in 5 days in buffer containing 25.5% PEG 8000, 0.12 M Ammonium Sulfate, 0.085 M Na Cacodylate trihydrate, pH 6.5, 15% v/v glycerol.

Crystallographic data was collected to 2.7 Å on beamline 14-1 at the Stanford Synchrotron Radiation Lightsource (SSRL). Data were processed using HKL2000. The crystal belongs to space group P 3121 and contains one molecule in the asymmetric unit. The structure was solved by molecular replacement using apoHip1 as a search model (PDB ID 5UNO). Final refinement involved positional, individual b-factor, and TLS refinement utilizing secondary structure restraints and reference model restraints using apoHip1 (PDB ID 5UNO) as a reference model. Phaser-MR and Phenix.refine as implemented in the PHENIX software package was used for molecular replacement and refinement, respectively. Model building was performed using Coot. Structure validation was performed using Molprobity.

Example 3. Minimum Inhibitory Concentration (MIC) Against *M. tuberculosis*

MICs were performed as described in Ollinger et al., 2013. Briefly, *M. tuberculosis* H37Rv expressing DsRed (Caroll et al., 2018) was grown in Middlebrook 7H9 medium containing 10% OADC (oleic acid, albumin, dextrose, catalase) supplement (Becton Dickinson) and 0.05% w/v Tween 80 (7H9-Tw-OADC) under aerobic conditions. Log phase bacteria was inoculated in assay plates containing compounds at a highest concentration of 200 μM using a 10-point two-fold serial dilution in 2% DMSO final concentration. Bacterial growth was measured by OD and RLU after 5 days of incubation at 37° C. The MIC was defined as the minimum concentration required for complete inhibition of growth.

Example 4. Intracellular *M. tuberculosis* Activity

*M. tuberculosis* H37Rv constitutively expressing DsRed (Caroll et al., 2018) was grown in Middlebrook 7H9 medium containing 10% v/v OADC (oleic acid, albumin, dextrose, catalase) supplement (Becton Dickinson) and 0.05% w/v Tween 80 (7H9-Tw-OADC) at 37° C. under aerobic conditions until log phase. Intracellular *M. tuberculosis* activity of inhibitor compounds was determined as described in (Manning et al., 2017). Briefly, RAW 264.7 cells were infected with log phase *M. tuberculosis* H37Rv constitutively expressing DsRed at a MOI of 1 for 24 hr at 37° C. in a humidified 5% CO, incubator. Infected cells were washed, harvested and inoculated in assay plates containing compounds and incubated for 3 days at 37° C. in a humidified 5% CO, incubator. Compounds were assayed at a highest concentration of 100 μM using a 10-point three-fold serial dilution in 1% DMSO final concentration. The cellular dye SYBR Green I (10,000×, Thermo Fisher) was added to assay plates at 5× final concentration and plates were imaged using an automated ImageXpress Micro XLS High Content Screening System (Molecular Devices) using FITC and Texas Red channels at 4× magnification. Raw data was normalized to negative control (1% DMSO) and expressed as % growth inhibition.

Example 5. Activity and Low Toxicity in Cellular Assays

Cells were seeded in plates and incubated overnight in a humidified incubator at 37° C., 5% $CO_2$. Inhibitor compounds were added 24 hours post cell seeding to cells at a highest concentration of 100 μM using a 10-point three-fold serial dilution in 1% DMSO final concentration. After 72-hours of incubation, CellTiter-Glo® reagent (Promega) was added to plates and the relative luminescent units (RLU) were measured using a Synergy 4 plate reader (Biotek). Raw data were normalized using the average RLU value from negative control (1% DMSO) and expressed as % growth. Growth inhibition curves were fitted using the Levenberg-Marquardt algorithm. The IC50 was defined as the compound concentration that produced 50% of the growth inhibitory response.

We claim:

1. A compound for the inhibition of a Hydrolase important for pathogenesis (Hip1) enzyme, the compound comprising:
- a tripeptide targeting sequence, that directs the compound to the active site of Hip1, the tripeptide targeting sequence comprising the sequence Phe-Lys-Leu in the N-terminal to C-terminal direction; and
- a C-terminal group conjugated to the Leu of the targeting sequence, the C-terminal group comprising
  - (i) an alpha-keto methyl ester electrophilic warhead configured to inactivate the Hip1 enzyme, or
  - (ii) a chromophore or fluorophore reporter group.

2. The compound of claim 1, further comprising a protecting group attached to the Phe of the tripeptide targeting sequence.

3. The compound of claim 2, wherein the protecting group comprises a benzyloxycarbonyl (Cbz) group.

4. The compound of claim 1, wherein the C-terminal group comprises the alpha-keto methyl ester electrophilic warhead and wherein the compound comprises the structure:

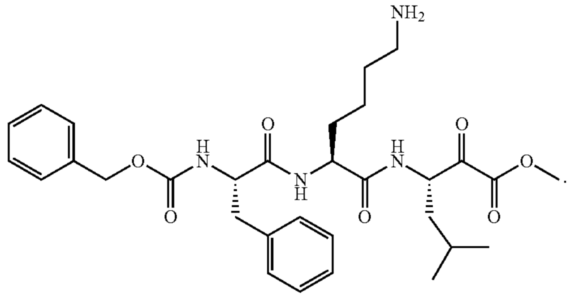 [SMILES: COC(=O)C(=O)[C@H](CC(C)C)NC(=O)[C@H](CCCCN)NC(=O)[C@H](Cc1ccccc1)NC(=O)OCc1ccccc1]

5. The compound of claim 1, wherein the C-terminal group comprises the chromophore or fluorophore reporter group.

6. The compound of claim 5, wherein the chromophore or fluorophore reporter group comprises a paranitroanilide (pNa) and wherein the compound comprises the structure:

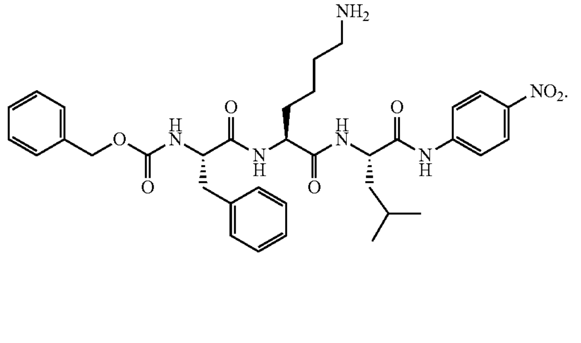 [SMILES: CC(C)C[C@H](NC(=O)[C@H](CCCCN)NC(=O)[C@H](Cc1ccccc1)NC(=O)OCc1ccccc1)C(=O)Nc1ccc([N+](=O)[O-])cc1]

7. A diagnostic assay for detecting the presence of *Mycobacterium tuberculosis* (Mtb), comprising the compound of claim 5.

8. A pharmaceutical composition for treating tuberculosis, comprising the compound of claim 1.

9. A complex comprising the compound of claim 1 bound to Hip1.

10. A vaccine composition comprising the compound of claim 1.

11. The vaccine composition of claim 10, wherein the vaccine composition is a booster to a *Bacillus* Calmette-Guérin (BCG) vaccine.

12. A compound for the inhibition of a Hydrolase important for pathogenesis (Hip1) enzyme, the compound comprising:
- a tripeptide comprising the sequence Phe-Lys-Leu in the N-terminal to C-terminal direction; and
- a C-terminal group conjugated to the Leu of the tripeptide, the C-terminal group comprising
  - (i) an alpha-keto methyl ester, or
  - (ii) a reporter group.

13. The compound of claim 12, further comprising a protecting group attached to the Phe of the tripeptide.

14. The compound of claim 12, wherein the C-terminal group comprises the reporter group.

15. The compound of claim 14, wherein the reporter group comprises a chromophore or fluorophore.

16. A diagnostic assay for detecting the presence of *Mycobacterium tuberculosis* (Mtb), comprising the compound of claim 14.

17. A pharmaceutical composition for treating tuberculosis, comprising the compound of claim 12.

18. A vaccine composition comprising the compound of claim 12.

19. The vaccine composition of claim 18, wherein the vaccine composition is a booster to a *Bacillus* Calmette-Guérin (BCG) vaccine.

20. A compound for the inhibition of a Hydrolase important for pathogenesis (Hip1) enzyme, the compound comprising:
- a tripeptide comprising the sequence Phe-Lys-Leu in the N-terminal to C-terminal direction; and
- a C-terminal group conjugated to the Leu of the tripeptide, the C-terminal group comprising
  - (i) an alpha-keto methyl ester, and the compound comprising the structure:

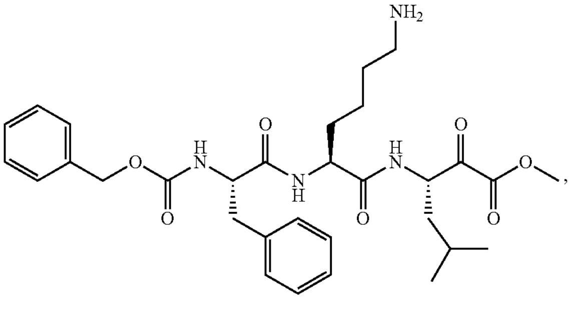 [SMILES: COC(=O)C(=O)[C@H](CC(C)C)NC(=O)[C@H](CCCCN)NC(=O)[C@H](Cc1ccccc1)NC(=O)OCc1ccccc1]

or

- (ii) a paranitroanilide (pNa) reporter group, and the compound comprising the structure:

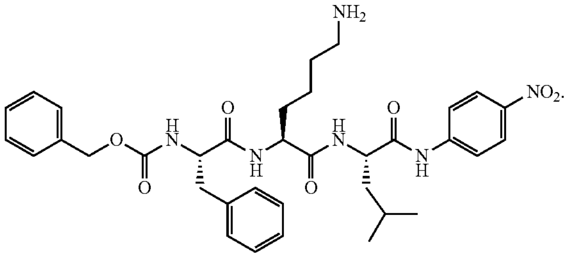 [SMILES: CC(C)C[C@H](NC(=O)[C@H](CCCCN)NC(=O)[C@H](Cc1ccccc1)NC(=O)OCc1ccccc1)C(=O)Nc1ccc([N+](=O)[O-])cc1]
* * * * *